United States Patent [19]
Masuda

[11] Patent Number: 5,172,347
[45] Date of Patent: Dec. 15, 1992

[54] TIME DISPLAYING APPARATUS

[75] Inventor: Isamu Masuda, Fukuoka, Japan

[73] Assignee: Nihonkenkozoshinkenkyukai Co., Ltd., Fukuoka, Japan

[21] Appl. No.: 474,106

[22] PCT Filed: Apr. 10, 1989

[86] PCT No.: PCT/JP89/00387
§ 371 Date: Apr. 23, 1990
§ 102(e) Date: Apr. 23, 1990

[87] PCT Pub. No.: WO90/06788
PCT Pub. Date: Jun. 28, 1990

[30] Foreign Application Priority Data
Dec. 15, 1988 [JP] Japan ............... 63-317287

[51] Int. Cl.$^5$ .............. G04B 47/06; 461N 1/00
[52] U.S. Cl. ................... 368/10; 368/11; 128/362; 128/783; 128/804
[58] Field of Search ......... 368/10, 11, 82, 239; 219/10.55 R, 400; 128/1.3–1.5, 362, 422, 783, 804

[56] References Cited
U.S. PATENT DOCUMENTS

| 4,615,179 | 10/1986 | Chiu et al. | 62/129 |
| 4,733,363 | 3/1988 | Waterbury | 368/10 |
| 4,901,461 | 2/1990 | Edwards et al. | 362/276 |
| 4,923,681 | 5/1990 | Cox et al. | 422/116 |

FOREIGN PATENT DOCUMENTS

| 54-121099 | 9/1979 | Japan . |
| 59-79398 | 5/1984 | Japan . |
| 60-193459 | 10/1985 | Japan . |
| 61-191037 | 11/1986 | Japan . |

Primary Examiner—Vit W. Miska
Attorney, Agent, or Firm—Jordan and Hamburg

[57] ABSTRACT

A time displaying apparatus is constituted in a manner that when a temperature sensor 54 or 55 installed in an electric appliance is turned on, a display controlling part changes-over the displaying operation by the numeric display 50 to a blinking operation, and thereby informs the user of that the electric appliance has risen in temperature above a predetermined value. Conventionally this kind of information is performed using an alarm buzzer or an alarm lamp, but in accordance with the present invention, such a special alarm component can be dispensed with, and there is no fear of incurring an increase in the number of parts and a rise in the cost.

6 Claims, 9 Drawing Sheets

TIME DISPLAYING APPARATUS

TECHNICAL FIELD

The present invention relates to a time displaying apparatus used for displaying a lapse of set time, for example, for an electric appliance wherein an operation time is set.

TECHNICAL BACKGROUND

Formerly, the present inventor has made a product a magnetic field generating apparatus for medical treatment which has a plurality of connected synthetic resin case bodies, wherein a magnetic field generator that a coil bobbin is disposed on an iron core is housed. This apparatus is such in which the magnetic field generator generates an alternating magnetic field when the coil bobbin is energized, and an effect of a magnetic medical treatment is obtained in a manner that one of plate surfaces of the case body is brought in contact with the surface of a human body, and the above-mentioned alternating magnetic field acts on an exterior magnetic field to act externally from this plate surface.

In this magnetic field generating apparatus for medical treatment, an operation time is set by a timer, and after a lapse of the set time, the operation stops automatically to terminate the medical treatment. This lapse of the set time (for example, the residual time) is displayed on a numeric display, and the user can devote himself to the medical treatment wile making sure of the numeric value on the numeric display as required.

Then, in the above-mentioned magnetic field generator, the surface temperature is raised by energizing the coil bobbin, and this heat can be utilized effectively also for thermal therapy by transmitting it to the case body. However, a rise in the surface temperature of the magnetic field generator higher than required due to successive use for a long time generates a risk of burning, and as a countermeasure for this, the operation of the magnetic field generator is forcedly stopped when the above-mentioned surface temperature rises higher than a predetermined value, and the generator is made to wait until a proper temperature is restored.

In this kind of magnetic field generating apparatus for medical treatment, when the operation of the apparatus is stopped in the midst of medical treatment due to a rise in the temperature, the user might misunderstand that the apparatus has gone out of order, or might be mistaken that the operation has been stopped after the set time has elapsed. To avoid such a misunderstanding or mistake, a rise in the temperature can be identified by incorporating an alarm buzzer or an alarm lamp, but this has problem of necessitating a special alarm component, increasing the number of parts and raising the manufacturing cost of the apparatus.

The present invention has been achieved in light of the above-mentioned problems, and purposes to provide a time displaying apparatus capable of advising of a rise in the temperature without using a special alarming component by informing a rise in the temperature by effectively using a numeric display displaying the lapse of time.

SUMMARY OF THE INVENTION

The present invention is directed to a time displaying apparatus for displaying a lapse of set time on a numeric display for an electric appliance wherein an operation time is set which comprises the temperature sensor installed in a diving part of the above-mentioned electric appliance and a display controlling part changing-over displaying operation to blinking operation when the temperature sensor is turned on.

In accordance with the present invention, the numeric display displays a lapse of set time during the operation of the electric appliance, but when the temperature sensor is turned on, the displaying operation of the lapse of time is changed-over to a predetermined blinking operation, and therefore the user can realize the occurrence of a rise in the temperature of the electric appliance higher than a predetermined value by watching this display.

Accordingly, a rise in the temperature can be indicated without using a special alarming component such as an alarm buzzer or an alarm lamp, and therefore there is no risk of incurring an increase in the number of parts and a rise in the cost.

THE PREFERRED EMBODIMENT OF THE INVENTION

Figure 1:
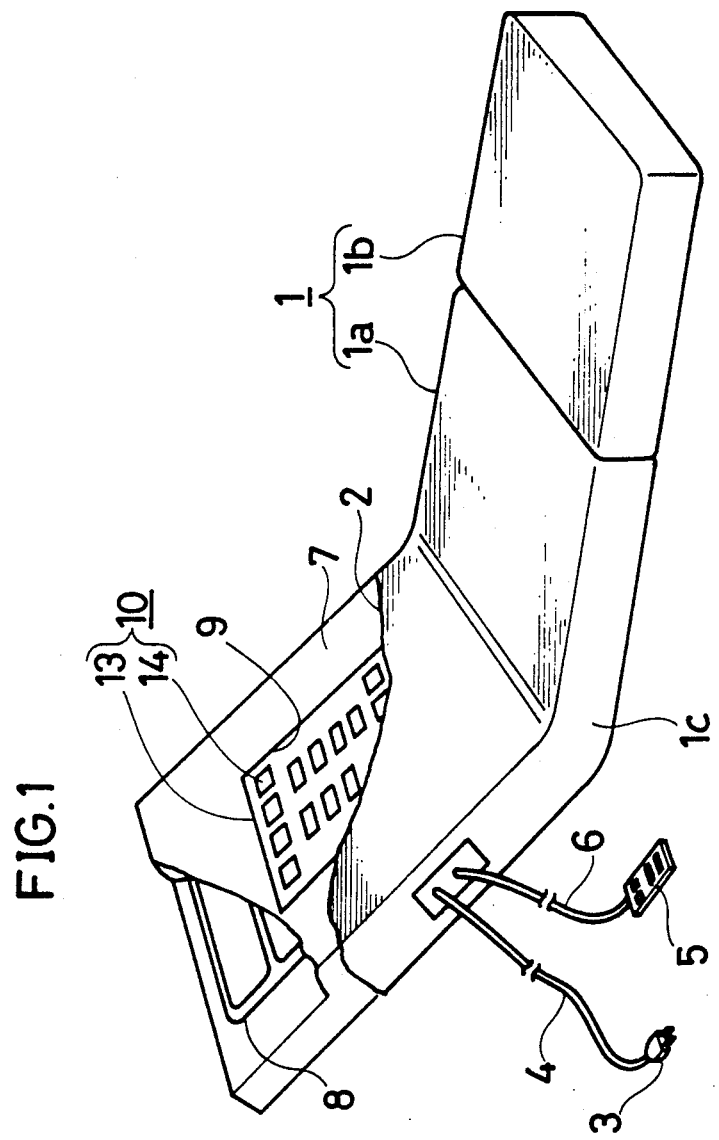
FIG. 1 is a partly-broken away perspective view showing a mat whereto the present invention is applied.

FIG. 1 shows a mat for magnetic therapy embodying the present invention. In this structure a mat main body is covered with a cloth cover 2, and on one of the side end surfaces, a power cord 4 provided with a plug 3 at the tip thereof and a lead-out wire 6 is provided with an operation board 5 at the tip thereof.

The whole of the mat main unit 1 is comprised of a cushion member 7 such as of urethane foam, a tip part 1b of which can be folded onto a main body part 1a. The main body part 1a supports the human body ranging from the head to the waist and legs, and the tip part 1b supports the tips of feet of the human body. A metal pipe 8 forming the frame of the mat is embedded in the cushion member 7 of the main unit part 1a, and a commercially known joint mechanism (not illustrated) capable of angular adjustment is installed at the lengthwise center part of the metal pipe 8, and thereby a joint part 1c is formed.

Figure 2:
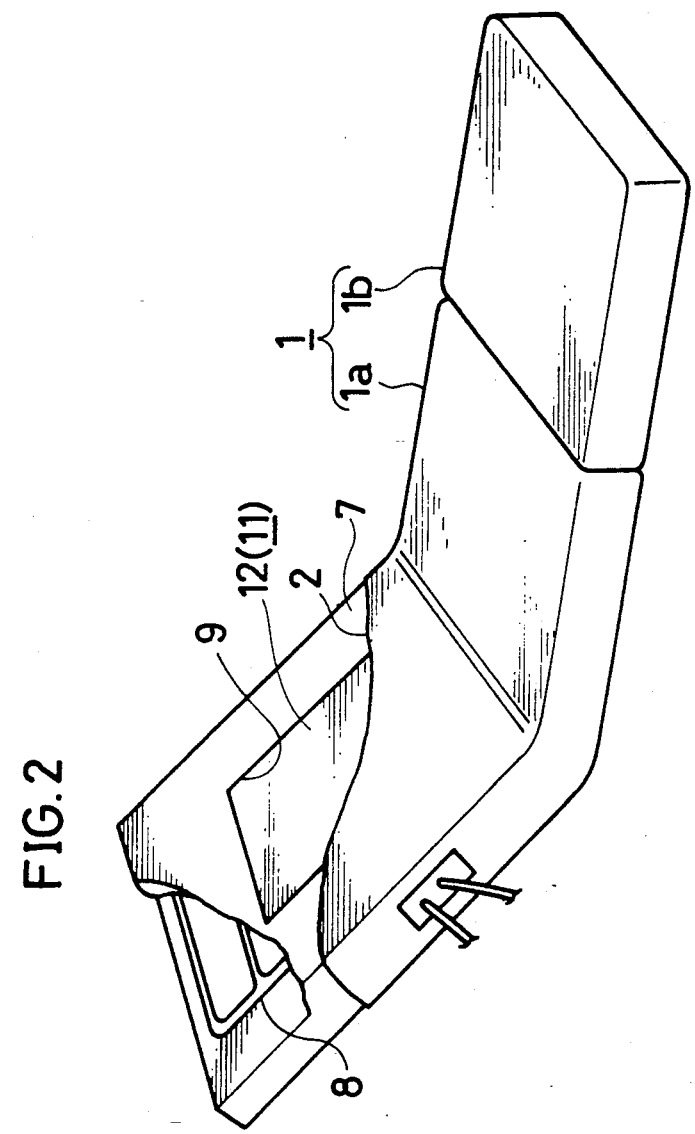
FIG. 2 is a partly-broken away perspective view showing another example of using the mat in FIG. 1.

In the cushion member 7 of the main body part 1a, a rectangular recess 9 is open upward at the position corresponding to the back-touching part, and a first attachment member 10 is fitted into this recess 9. The member 10 may be substituted by a second attachment member 11, as shown in FIG. 2, as required.

Each of the first and the second attachment members 10 and 11 has a shape corresponding to the recess 9, and in the fitted state into the recession 9, the top surface of each of the attachment members 10 and 11 and the top surface of the cushion member 7 lie in the same plane.

The second attachment member 11 consists only of a cushion member 12. This cushion member 12 desirably uses the same material as the cushion member 7 of the main body part 1a to eliminate a feel of incongruity.

Figure 3:
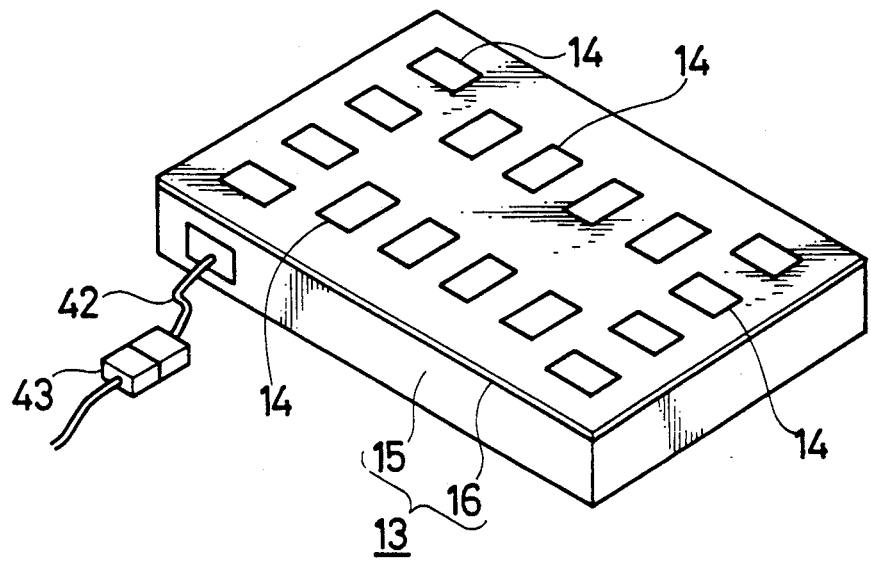
FIG. 3 is a perspective view showing a first attachment member attached to the mat.

The first attachment member 10 has a structure in which a plurality of sets of magnetic field generating apparatuses 14 for medical treatment are embedded in a cushion material 13. As shown in FIG. 3, a die-hole part (not illustrated) is installed between a cushion base member 15 and a cushion lid member 16, and a plurality of sets of magnetic field generating apparatuses 14 for medical treatment are fitted into and supported by this part. The magnetic field acting surface (as described later) of each magnetic field generating apparatus 14 for medical treatment is exposed above the cushion lid member 16. The cushion base member 15 and the cushion lid member 16 are formed for rubber or urethane foam, but the cushion lid member 16 desirably uses the same material as the cushion member 7 of the main unit part 1a to eliminate the giving of a feel of incongruity given to the human body.

Figure 4:
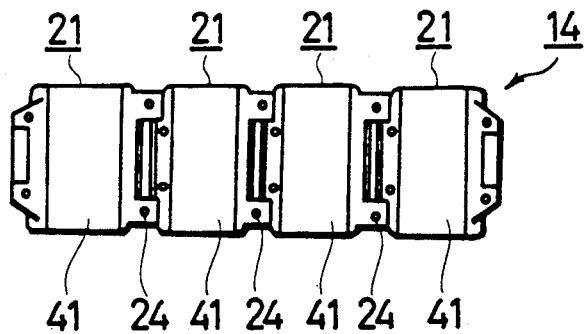
FIG. 4 is a front view showing a magnetic field generating apparatus for medical treatment incorporated in the first attachment member.
Figure 5:
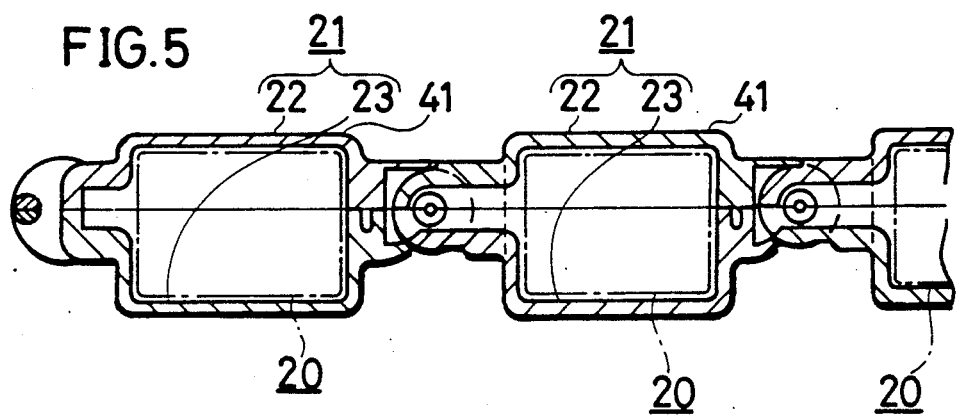
FIG. 5 is a horizontally-cut cross-sectional view of the magnetic field generating apparatus for medical treatment.
Figure 6:
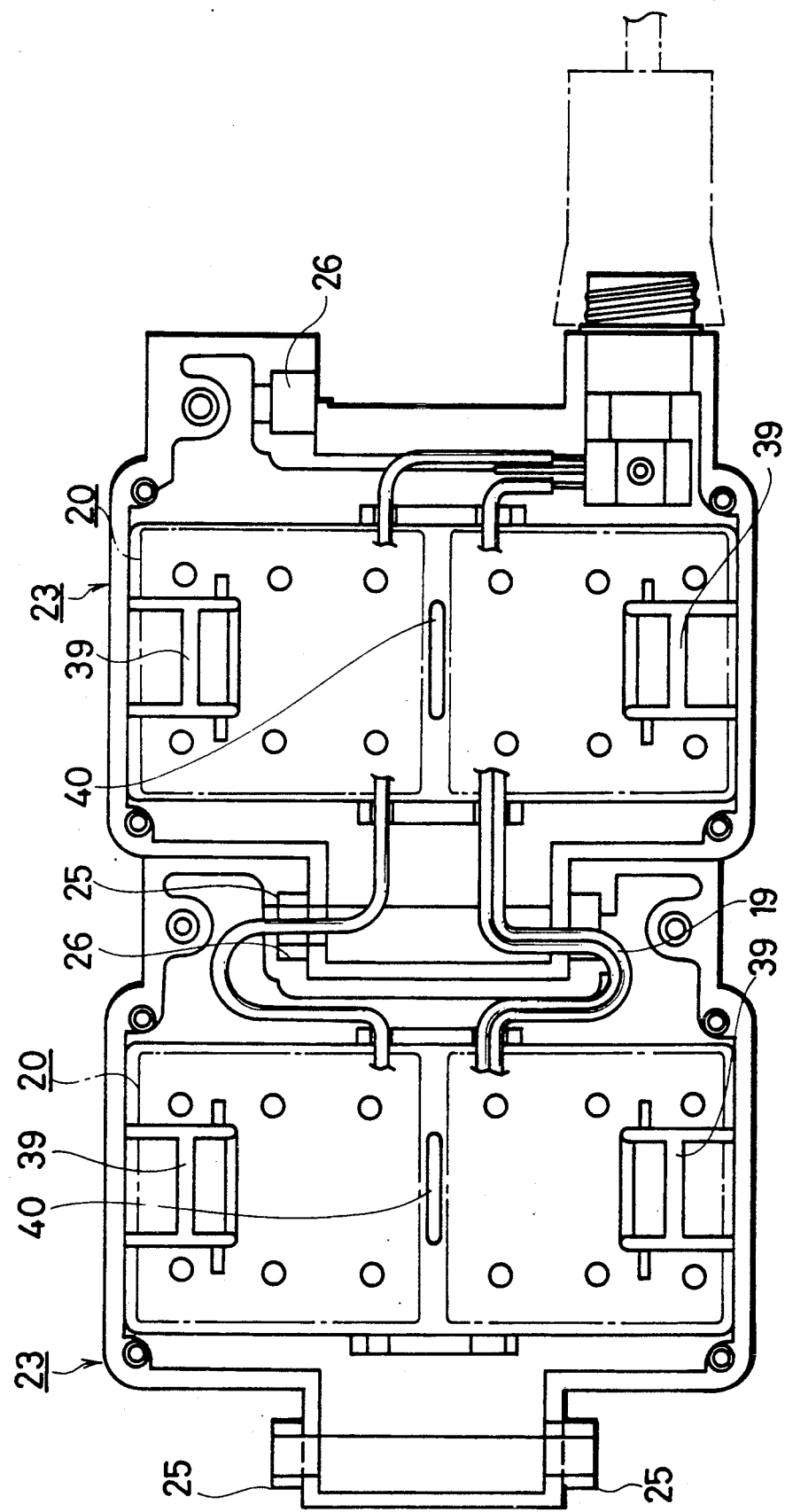
FIG. 6 is a plan view showing one of half-bodies of the case as viewed from the inside.

Each above-mentioned magnetic field generating apparatus 14 for medical treatment, as shown in FIG. 4 through FIG. 6, has a structure in which a magnetic field generator 20 is disposed in each of a plurality of synthetic resin cases 21, and the respective case bodies are pivot-connected in one line in a manner capable of bending mutually.

Each case body 21 is formed in a manner that the open surfaces of paired half-bodies of case 22 and 23 butt against one another and are fixed at a plurality of positions by screws 24. On side end surface of each case body 21, either protruded shafts 25 and 25 in the up-down direction or bearing holes 26 and 26 are formed, and the protruded shaft 25 is engaged with the bearing hole 26 between the adjacent case bodies 21 and 21. The thereby the adjacent case bodies 21 and 21 are pivotally-connected in a manner capable of bending and rotating mutually.

Figure 7:
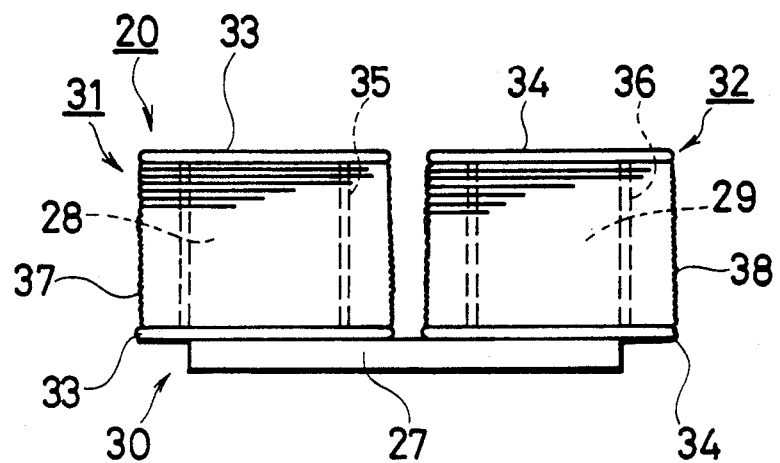
FIG. 7 is a front view showing the external appearance of a magnetic field generator.

As shown in FIG. 7, the above-mentioned magnetic field generator 20 consists of a laminated iron core 30 provided with legs 28 and 29 at both ends of a base 27 and coil bobbins 31 and 32 fitted to the legs 28 and 29. Each of the coil bobbins 31 and 32 has a structure in which coils 37 and 38 are wound around the peripheral surfaces of spools 35 and 36 having collars 33 and 34 at the both ends thereof, and when an alternating current flows through each of the coils 37 and 38, an alternate magnetic field is generated from the tips of the legs 28 and 29.

As shown in FIG. 6, on the inner surface of one of the above-mentioned half-bodies of case 23, positioning pieces 39 and 39 for positioning the magnetic field generator 20 and a protruded rod 40 for supporting the magnetic field generator 20 are formed integrally in a protruded fashion. The bottom surface of the base 27 is supported by the protruded rod 40.

On the inner surface of the other half-body of case 22, recesses (not illustrated) wherein each one of the collars 33 and 34 of the above-mentioned spools 35 and 36 is fitted are installed, and the plate surface of the half-body of case 22 comprising these recesses functions as a magnetic field acting surface 41.

Figure 8:
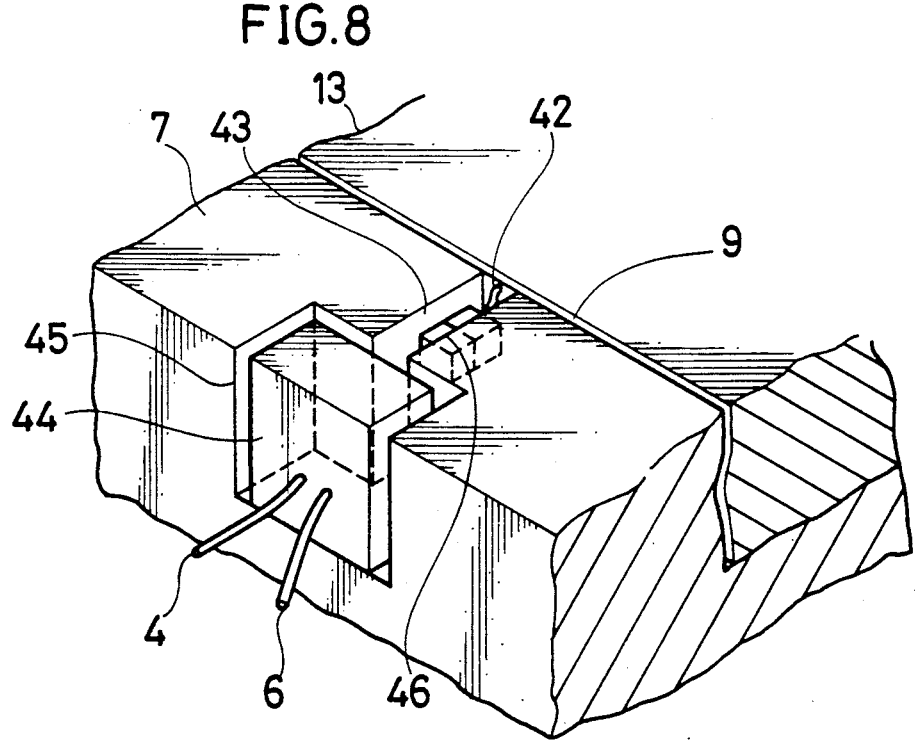
FIG. 8 is an enlarged perspective view showing part of the first attachment member.

The four magnetic field generators 20 are electrically connected in parallel by a lead 19, and the four sets of magnetic field generating apparatus for medical treatment are electrically connected in parallel. As shown in FIG. 3 and FIG. 8, an electrical connecting cord 42 is led-out from one side surface of the cushion member 13, being further led-out to a terminal box 44 through a connector 43. The above-mentioned power code 4 and lead-cut wire 6 are led from this terminal box 44. The above-mentioned connector 43 is provided for connecting/disconnecting each magnetic field generating apparatus for medical treatment 14 to/from the power supply in attaching/detaching the first attachment member 10 to/from the above-mentioned recession 9, and is always positioned in a groove 46 installed between the recess 9 and a terminal box housing part 45. The opening of the groove is closed as required with a cushion lid (not illustrated).

Figure 9:
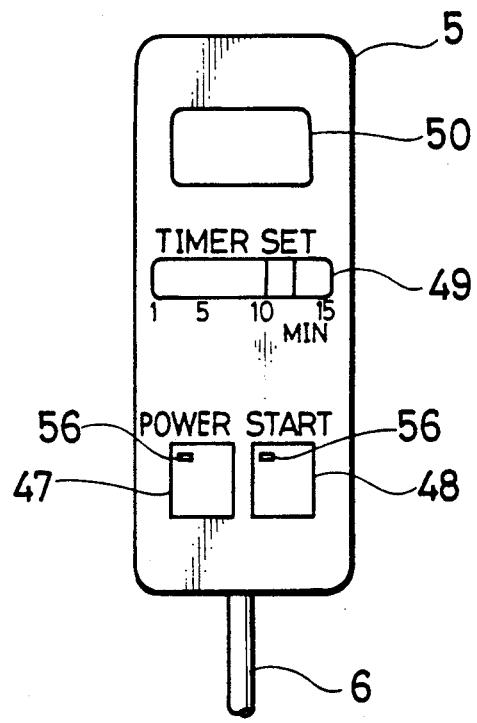
FIG. 9 is a front view showing a configuration of an operation board.

FIG. 9 shows the operation board 5 at the tip of the lead-out wire 6. The board surface thereof has a power button 47 for turning on power, a start button 48 for starting a timer, a time setting unit 49 for setting the time of the timer, and a numeric display 50 for displaying a residual time of the timer.

Figure 10:
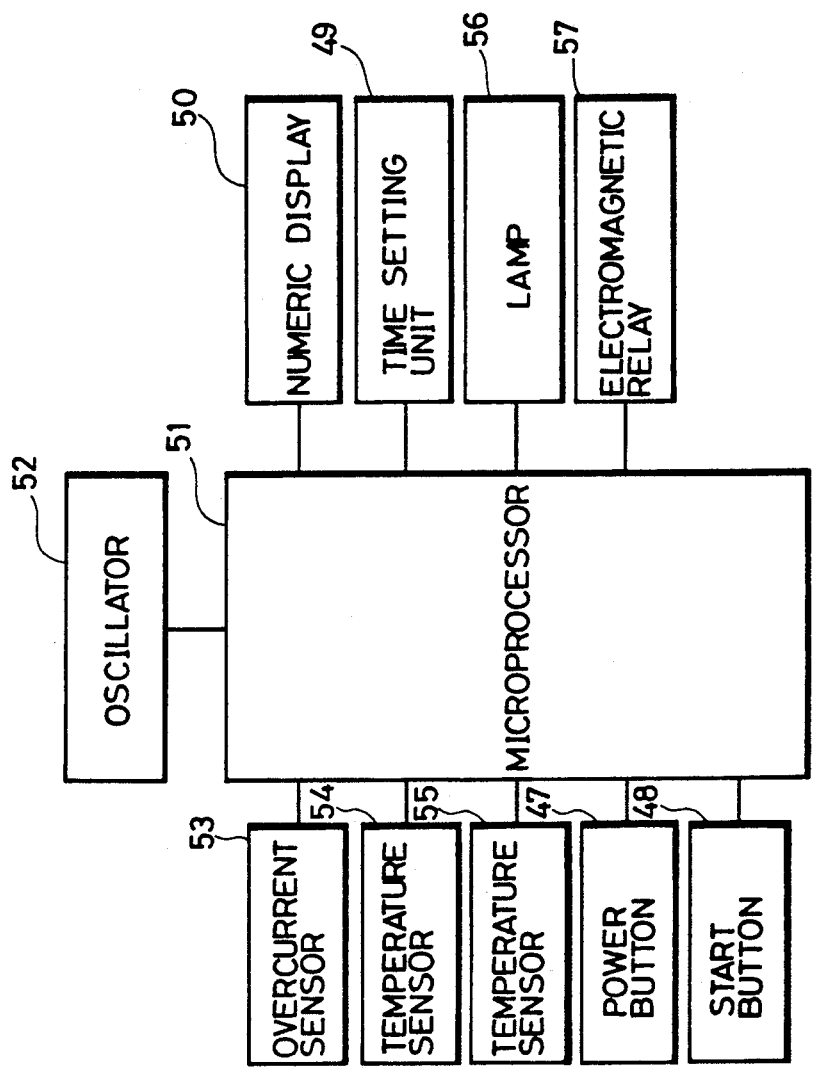
FIG. 10 is a block diagram showing an example of a circuit configuration of a control unit.

FIG. 10 shows an example of circuit configuration of a control unit for controlling the operation of the above-mentioned magnetic field generating apparatus for medical treatment.

This control unit has an overcurrent sensor 53, temperature sensors 54 and 55, the power button 47, the start button 48, the numeric display 50, the time setting unit 49, lamps 56, an electromagnetic relay 57 and the like, connected electrically to a microprocessor 51 which is incorporated in the above-mentioned operation board 5 and is a main unit of control and arithmetic operation. In FIG. 10, an oscillator 52 generates a clock signal and gives it to the microprocessor 51.

The overcurrent sensor 53 detects whether or not a current larger than a rated value has passed through this magnetic field generating apparatus for medical treatment 14. The two temperature sensors 54 and 55 are, for example, bimetals, and one of the temperature sensors 54 is installed at a proper place of the iron core 21 of each magnetic field generator 20. The other temperature sensor 55 is installed at a proper place of the power transformer in the operation board 5. These sensors detect that the surface temperatures of the iron core 21 and the power transformer have risen to predetermined temperatures, respectively. The power button 47, the start button 48, the numeric display 50 and the time setting unit 49 are disposed on the board surface of the operation board 5, and function respectively as mentioned above. The lamps 56 are installed in the power button 47 and the start button 48, and are lit by pushing these buttons. An electromagnetic relay 57 is actuated when the overcurrent sensor 53 or either of the temperature sensors 54 and 55 is turned on, and opens a contact in the passage circuit to each magnetic field generator 20 to stop energizing.

Figure 11:
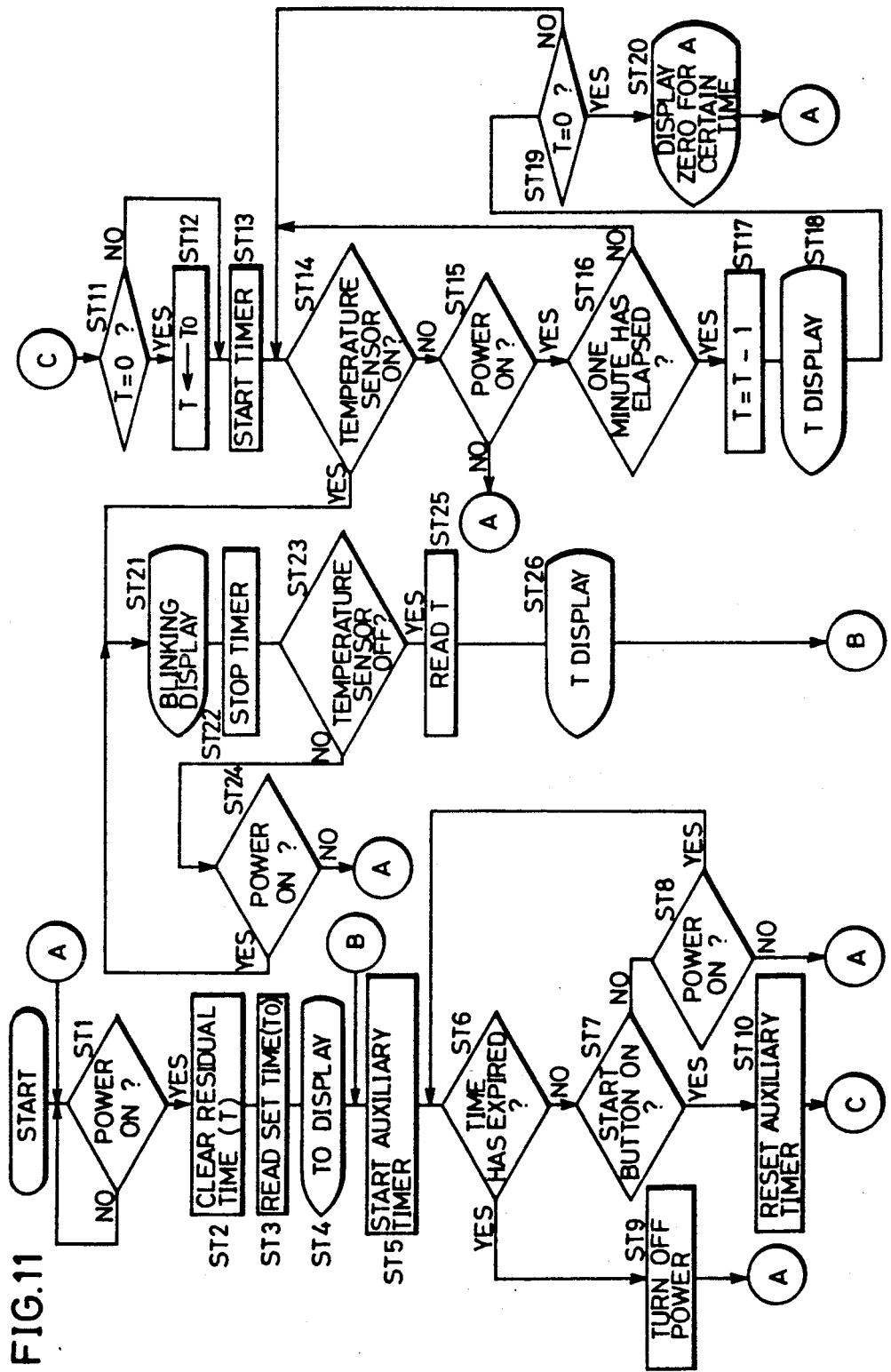
FIG. 11 is a flow chart showing controlling procedures of the control unit.

FIG. 11 shows controlling procedures of the above-mentioned microprocessor 51, and in step 1 in FIG. 11 (shown by "ST1" in the figure), judgment is made on whether or not the power button 47 has been pushed.

When this power button 47 is pushed, power is supplied to the control unit, and the microprocessor 51 clears the inner memory area for storing a residual time (step 2). Next, the microprocessor 51 reads a set time $T_0$ from the time setting unit 49, and stores it in the corresponding inner memory area, and thereafter makes the numeric display 50 display the set time $T_0$ as the residual time T (steps 3 and 4).

In the next step 5, an auxiliary timer in the microprocessor 51 starts, and in the subsequent steps 6 and 7, a check is made of whether or not the start button 48 has been pushed before time expiration. Steps 6, 7 and 8 show the state of waiting for a pushing operation of the start button 48, and if the auxiliary timer expires, processing moves from step 6 to step 9, turns off power, and returns to the initial waiting state.

If the start button 48 is pushed before expiration of the auxiliary timer, the auxiliary timer is reset in step 10, and subsequently in step 11, a judgment is made of whether or not the residual time T is zero. In this case, the residual time T has been cleared in step 2, and therefore the judgment in step 11 results in "YES", and in the next step 12, the set time $T_0$ is set in a predetermined memory area as the residual time T, and in the next step 13, the timer in the microprocessor 51 starts to count time.

In the next step 14, a judgment is made of whether or not either of the temperature sensors 54 and 55 has been turned on due to a temperature rise above a predetermined value, and if the judgment results in "NO", in the next step 15, it is made sure that the power button 47 is in on-state, and in the next step 16, whether or not one minute has elapsed is judged. Thus, when one minute has elapsed, the judgment in step 16 results in "YES", and one minute is subtracted from the residual time T, and the content of the numeric display 50 is renewed (steps 17 and 18). Subsequently in step 19, whether or not the residual time T is zero is checked, and if it is not zero, processing returns to step 14, and similar processing is repeated.

In addition, when the residual time T is judged to be zero in step 19, processing proceeds to step 20, and zero is displayed on the numeric display 50 for a certain time, and thereafter processing returns to the initial waiting state.

Now, assuming that any one of the magnetic field generators 20 excessively rises in temperature, the corresponding temperature sensor 54 is turned on, and the judgment in step 14 results in "YES". In this case, predetermined numerals (for example, "888") are displayed on the numeric display 50, and the numerals blink to inform the user of that the temperature has risen. When such a state takes place, the microprocessor 51 energizes the electromagnetic relay 57 to open the contact, and thereby stops energizing of each magnetic field generator 20, and steps the counting operation of the timer (step 22).

The temperature is reduced by stopping energizing, but in steps 23 and 24, the microprocessor 51 waits for restoration of the temperature sensor 54 to the original off-state due to this reduction in the temperature.

Thus, when the temperature sensor 54 is turned off, the microprocessor 51 reads the residual time T in step 25, and makes the numeric display 50 display the residual time T in place of the blinking display in the subsequent step 26. Thereafter it returns to step 5, and actuates the auxiliary timer, and waits for a pushing operation of the start button 48 for continuing the operation before time expiration.

In addition, when the operation is continued, the residual time T is not zero, and therefore the residual time T is not zero, and therefore the judgment in step 11 results in "NO", and step 12 is skipped over, and processing proceeds to step 13.

Figure 12:
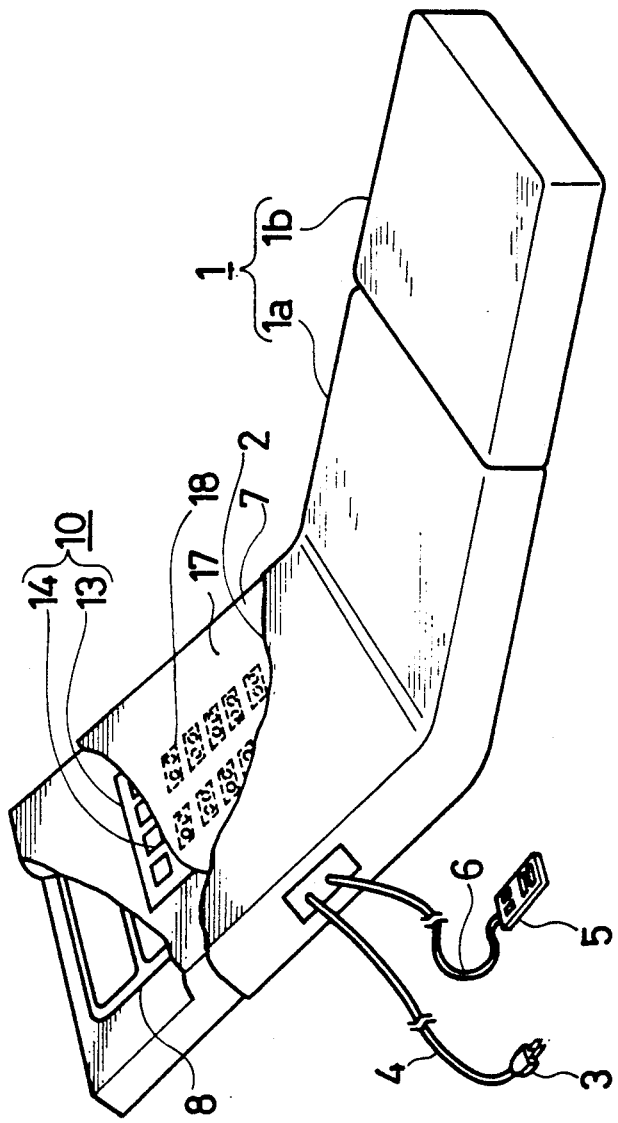
FIG. 12 is a partly-broken away perspective view showing another example of the mat to which the present invention is applied.

FIG. 12 shows a second embodiment of the present invention.

This embodiment has a structure in which a sheet member 17 is superposed on the mat main body 1 and the whole thereof is covered with the cloth cover 2. Permanent magnets 18 are disposed on the sheet member 17 at the position corresponding to the magnetic field generating apparatus for medical treatment 14. In accordance with this embodiment, when the magnetic field generating apparatus for medical treatment 14 is operated, the permanent magnets 18 are vibrated by the alternating magnetic field thereof, and therefore it can give a moderate massaging action on the human body.

In addition, in the above-mentioned embodiments, the examples wherein the present invention is applied to the magnetic field generating apparatus for medical treatment are shown, but the present invention can be applied also to any electric appliance having a danger of rise in the temperature without being limited to the above-described cases.

Also, in the above-mentioned embodiment, a rise in the temperature is indicated by displaying a predetermined numeric value on the numeric display 50 and making this display blink, but this rise can be indicated also by another displaying method such that the blinking operation is performed with the residual time displayed intact.

When the mat having the above-mentioned configuration is used for medical treatment, the power-supplied state is set by pushing the power button 47 on the operation board 5, and a time of the timer is set by slide-operating the knob of the time setting unit 47, and thereafter the respective magnetic field generating apparatuses for medical treatment 14 are started all together. Thereby, an alternating magnetic field is generated from each magnetic field generator 20 of each magnetic field generating apparatus for medical treatment 14, and this magnetic field acts on the human body on the mat.

If the magnetic field generator 20 or the power transformer rises in temperature higher than a predetermined value and the temperature sensor 54 or 55 is turned on, the operation of the magnetic field generating apparatus for medical treatment 14 is stopped, and the operation of the numeric display 50 is changed-over from the displaying operation of the residual time to the blinking operation of predetermined numerals, and the user is informed of that the temperature has risen unusually.

Thus, when the temperature is restored to a proper state by stopping the operation, the medical treatment can be resumed by operating the operation board 5, and thereafter, when the set time has elapsed, the operation of each magnetic field generating apparatus for medical treatment 14 stops automatically, and the medical treatment is completed.

In addition, after completing the medical treatment, the cover 2 is opened, the first attachment member 10 is taken out from the recess 9 of the mat main body 1, and the second attachment member 11 is fitted into it. Thereby this mat can be used as a normal mat.

What is claimed is:

1. A magnetic field generating apparatus for medical treatment of a person, comprising:

magnetic field generator means for generating a magnetic field for medical use;

support means for supporting said magnetic field generator means;

time displaying means for displaying a lapse of a set time on a numeric display wherein an operation time is set, the time displaying means including:

numeric time display means for displaying the lapse of said set time, temperature sensing means for sensing the temperature of said magnetic field generator means, and display controlling means for changing over a time displaying operation on said numeric time display to a blinking operation when the temperature sensing means senses a temperature exceeding a predetermined temperature.

2. A magnetic field generating apparatus in accordance with claim 1, wherein said magnetic field generator means includes a coil, means for generating an alternating magnetic field by energizing said coil, and a power transformer, and wherein the temperature sensing means comprises first temperature sensor means for sensing the temperature of said magnetic field generator means and second temperature sensor means for sensing the temperature of said power transformer.

3. A magnetic field generating apparatus in accordance with claim 1, further including an operation board for holding said numeric time display means, and a lead-out wire lead-out from the magnetic field generator means and connected with the operation board.

4. A magnetic field generating apparatus in accordance with claim 1, wherein said display controlling means includes a microprocessor.

5. A magnetic field generating apparatus in accordance with claim 1 or claim 4, wherein said display controlling means changes-over the displaying operation of said numeric time display means to a display operation displaying predetermined numerals on said numeric time display means and making said numerals blink when the temperature sensing means senses a temperature exceeding the predetermined temperature.

6. A magnetic field generating apparatus in accordance with claim 1 or claim 4, wherein said display controlling means comprises means for changing-over the displaying operation of said numeric time display means to a displaying operation displaying numerals showing a residual time on said numeric time display means and for making said numerals thereof blink when the temperature sensing means senses a temperature exceeding said predetermined temperature.

* * * * *